United States Patent
Julian Ibañez et al.

(10) Patent No.: US 10,383,698 B2
(45) Date of Patent: Aug. 20, 2019

(54) DEVICES AND KITS FOR ASSISTING IN OPEN SURGERIES

(71) Applicant: Fundacio Institut D'Investigacio En Ciencies De La Salut Germans Trias I Pujol, Badalona (ES)

(72) Inventors: Juan Francisco Julian Ibañez, Barcelona (ES); Jordi Navinés López, Barcelona (ES)

(73) Assignee: FUNDACIÓ INSTITUT D'INVESTIGACIÓ EN CIÈNCIES DE LA SALUT GERMANS TRIAS I PUJOL, Badalona (ES)

(*) Notice: Subject to any disclaimer, the term of this patent is extended or adjusted under 35 U.S.C. 154(b) by 0 days.

(21) Appl. No.: 15/740,636

(22) PCT Filed: Jun. 28, 2016

(86) PCT No.: PCT/EP2016/064960
§ 371 (c)(1),
(2) Date: Dec. 28, 2017

(87) PCT Pub. No.: WO2017/001379
PCT Pub. Date: Jan. 5, 2017

(65) Prior Publication Data
US 2018/0318034 A1 Nov. 8, 2018

(30) Foreign Application Priority Data

Jun. 29, 2015 (EP) .................................... 15382341

(51) Int. Cl.
*F21V 21/00* (2006.01)
*A61B 90/35* (2016.01)
(Continued)

(52) U.S. Cl.
CPC ...... *A61B 90/35* (2016.02); *A61B 17/320068* (2013.01); *A61B 18/1402* (2013.01);
(Continued)

(58) Field of Classification Search
CPC ......... A61B 90/30; A61B 90/35; A61B 90/50; A61B 2017/00057
(Continued)

(56) References Cited

U.S. PATENT DOCUMENTS

| 4,686,972 A | 8/1987 | Kurland |
| 5,450,293 A | 9/1995 | Hoffman |

(Continued)

FOREIGN PATENT DOCUMENTS

| CN | 202376066 U | 8/2012 |
| DE | 202015002844 U1 | 7/2015 |

(Continued)

OTHER PUBLICATIONS

International Search Report and Written Opinion dated Jan. 30, 2017 for PCT/EP2016/064960, 18 pages.

*Primary Examiner* — Laura K Tso
(74) *Attorney, Agent, or Firm* — Squire Patton Boggs (US) LLP (57) ABSTRACT

Various examples of devices and kits for assisting in and illuminating medical procedures are disclosed. The devices may be attached to handheld medical tools. Also disclosed are various examples of medical procedures that may be carried out using the devices or kits. Also discloses are various examples for mounting auxiliary medical tools to a device mounted on a primary medical tool.

21 Claims, 9 Drawing Sheets

(51) Int. Cl.
*G06F 3/0354* (2013.01)
*A61B 90/30* (2016.01)
*A61B 90/00* (2016.01)
*A61B 90/50* (2016.01)
*A61B 90/57* (2016.01)
*A61B 17/32* (2006.01)
*A61B 18/14* (2006.01)
*A61B 17/00* (2006.01)
*A61B 18/00* (2006.01)

(52) U.S. Cl.
CPC ............ *A61B 90/30* (2016.02); *A61B 90/361* (2016.02); *A61B 90/50* (2016.02); *A61B 90/57* (2016.02); *G06F 3/03542* (2013.01); *A61B 2017/00022* (2013.01); *A61B 2017/00057* (2013.01); *A61B 2017/00084* (2013.01); *A61B 2017/00477* (2013.01); *A61B 2018/00172* (2013.01); *A61B 2018/1412* (2013.01); *A61B 2090/0807* (2016.02); *A61B 2090/306* (2016.02); *A61B 2090/309* (2016.02); *A61B 2218/002* (2013.01); *A61B 2218/007* (2013.01); *A61B 2218/008* (2013.01)

(58) Field of Classification Search
USPC ..... 362/119, 120, 109; 606/13, 17; 600/245, 600/246, 248, 249
See application file for complete search history.

(56) References Cited

U.S. PATENT DOCUMENTS

| | | | | |
|---|---|---|---|---|
| 5,797,670 | A * | 8/1998 | Snoke | .................. B25B 23/18 24/16 PB |
| 7,393,114 | B2 * | 7/2008 | Devlin | .............. A61M 37/0076 362/109 |
| 2002/0022764 | A1 | 2/2002 | Smith et al. | |
| 2008/0281299 | A1 * | 11/2008 | Menn | .................. A61B 1/0014 606/1 |
| 2009/0005638 | A1 * | 1/2009 | Zwolinski | .......... A61B 1/00087 600/106 |
| 2009/0054890 | A1 * | 2/2009 | DeCarlo | ............ A61B 18/1402 606/34 |
| 2011/0063820 | A1 * | 3/2011 | Wang | ..................... B25B 23/18 362/120 |
| 2011/0090679 | A1 * | 4/2011 | Geuder | .................... A61B 1/07 362/183 |
| 2012/0035416 | A1 * | 2/2012 | Fernandez | ............... A61B 1/05 600/102 |
| 2012/0101497 | A1 | 4/2012 | Jayaraj | |
| 2012/0283718 | A1 * | 11/2012 | Cosmescu | .......... A61B 18/1402 606/33 |
| 2013/0197317 | A1 * | 8/2013 | Daniel | ................. A61B 1/0684 600/249 |
| 2013/0267787 | A1 * | 10/2013 | Warnock | ........... A61B 18/1402 600/249 |
| 2013/0303845 | A1 * | 11/2013 | Skula | ..................... A61B 1/018 600/104 |
| 2013/0331657 | A1 * | 12/2013 | Basson | .................. A61B 90/30 600/249 |
| 2014/0296629 | A1 * | 10/2014 | Chang | ................ A61B 1/00101 600/104 |
| 2015/0080933 | A1 * | 3/2015 | Igov | ............... A61B 17/320016 606/190 |

FOREIGN PATENT DOCUMENTS

| | | |
|---|---|---|
| EP | 1693021 A1 | 8/2006 |
| EP | 2027824 A1 | 2/2009 |
| EP | 2502553 A1 | 2/2012 |
| FR | 2066033 A5 | 8/1971 |
| WO | WO 2001/52716 A2 | 7/2001 |
| WO | WO 2004/054626 A2 | 7/2004 |
| WO | WO 2006/033671 A2 | 3/2006 |
| WO | WO 2007/038998 A1 | 4/2007 |
| WO | WO 2014/173932 A1 | 10/2014 |

* cited by examiner

DEVICES AND KITS FOR ASSISTING IN OPEN SURGERIES

This application claims benefit of European Patent Application no. 15382341.4 filed on Jun. 29, 2015.

The present disclosure relates to devices and kits for assisting in a medical procedure, particularly open surgeries.

BACKGROUND

Surgeries can generally be grouped in laparoscopic or minimally-invasive surgeries and open surgeries. In this sense, open surgeries should be understood as traditional surgeries which require a relatively long incision in order for the surgeon to insert instruments and visualize the surgery through the incision, whereas minimally-invasive surgeries are much less invasive and involve much smaller incisions. With an open approach, e.g. The incision for a typical appendectomy is approximately 10 cm (4 inches) long. While, using minimally-invasive techniques, the incisions may range from 0.5 to 1.5 cm (¼ to ½ inch) or for some surgeries even no incisions at all.

The key element in laparoscopic surgery is the use of a laparoscope, i.e. a long fiber optic cable system which allows viewing of the affected area. Laparoscopic surgeries belong to the field of endoscopy, i.e. using an endoscope which is an instrument used to examine the interior of a hollow organ or cavity of the body. In laparoscopic surgery, the surgeon is actually performing the surgery from outside the patient's body, removed from the actual intervention site. Surgical instruments are controlled from a distance and reach the intervention site through a tubular body, e.g. a catheter.

Illumination devices for illuminating medical procedures are known. Since practitioners in the several medical fields of specialization usually need enhanced visualization of a body tissue and/or body cavities, a variety of illumination systems have been designed to address this issue.

There are currently several ways to illuminate a medical procedure, such as e.g. open surgeries in an operating room. One option is overhead lighting mounted in a ceiling. Surgical lights may be fixed in the ceiling or be suspended from a ceiling with an arm that can be manipulated to reposition and reorient the light. However, these kinds of lighting usually provide a general and diffuse kind of illumination, which may lack the precision needed to point towards and adequately illuminate the desired target depending on the kind of intervention. The light may encounter obstacles that cast a shadow over said target, particularly in interventions in bodily cavities or openings.

Another option is the use of lighting devices held in a person's hand. In such a case, surgeons or other operating room personnel may employ handheld lighting devices, such as surgical flashlights. However, during the time that the surgeon is holding the device, his/her hand that is holding the lamp is unable to perform other actions. If instead such a device is held by other personnel, the accuracy in lighting the target might not correspond to the surgeon's specific demands. As a solution to overcome some of the aforementioned limitations, surgical headlights may be used. However, surgical headlights commonly are heavy, and can be uncomfortable. They also need positioning and possibly adjustments during surgery, again requiring a free hand to do so. Furthermore, the headlight and all related apparatus are unsterile, so that precautions must be taken in order to avoid contamination of the surgical field.

In a similar manner, during open surgeries practitioners usually need ways to indicate instruments, a body tissue and/or body cavities to other practitioners or personnel involved. Identification of the correct intervention point and the direction of a required movement (e.g., incision, needle advancement) can be of pivotal importance for completing these procedures. Verbal communication sometimes may not adequately provide the guidance. Laser pens are sometimes used for such indications.

In the course of an open surgery, many combinations of surgical instruments may be needed. For example, it is quite often that one or more blood vessels need to be severed in the course of an open surgery. In these cases, normally after introducing the scalpel the surgeon needs to provide means for closing and cauterizing such blood vessels. To do this, various surgical elements may be needed. Alternatively, it is known to use an electric scalpel or electric surgical pencil. This way, the blood vessels can be severed and cauterized in a single step. However, during cauterization smoke may hinder the view of the surgeon. Thus a further surgical instrument may be needed, namely a surgical smoke aspirator which will normally be operated by a surgical assistant.

Radio-guided surgery is also known, in which a patient is administered a radioactive material. The radioactive material concentrates e.g. in cancer cells. By using a radioactive probe, a tumor and affected tissue can be located and removed with precision. However, when the surgeon is holding the probe, his/her hands are unable to perform other actions. Thus normally the radioactive probe will be held/operated by a surgical assistant. Often both medical professionals cannot access the opening for the surgery at the same time, i.e. one person uses the radioactive probe to locate affected tissue and tells the surgeon where to cut.

Currently, many such combinations of surgical instruments, including, but not limited to, cutting, suturing, aspiration, clamping, cauterizing, irrigating, and various forms of tissue manipulation within a patient's body, may be needed simultaneously. And in all these and other combinations of surgical instruments for open surgery, visibility is very important, but often not ideal because more than one person is needed to handle different tools.

It is an object of examples of the present disclosure to provide alternative devices and kits for assisting in open surgeries, particularly for assisting or illuminating in open surgeries that at least partially overcome some of the aforementioned drawbacks.

SUMMARY

According to a first aspect, a device for assisting in an open surgery is provided. The device comprises: a base configured to be mounted on a portion of a handheld medical tool, an illumination device mounted on the base such that when the base is attached to the handheld medical tool, the illumination device is directed towards a distal end of the handheld medical tool. The device further comprises an appendage to the base having a receptacle configured to receive an auxiliary medical device.

According to this aspect, a device is provided which can be coupled to a handheld medical tool (e.g. an electrical scalpel) to improve visualization during open surgery, and at the same allow auxiliary devices to be coupled to the handheld medical tool.

Such an auxiliary device may be e.g. a surgical aspirator or smoke/liquid evacuator, a laser pointer, a handheld ultrasound system, an irrigator for electrocoagulation, a further illuminating device, a radioactive probe, a camera or a sensor among others.

In general, these devices may particularly be instruments that assist the surgeon while performing the surgery (e.g. interacting with the tissue) with the (principal) handheld medial tool.

No further medical personnel is needed to hold such an auxiliary device. The surgical procedure can thus be more effective, quicker and safer.

The attachment of the base with appendage locally increases the cross-sectional dimensions of the medical tool. However, in examples of the present disclosure, the base with appendage may remain outside the patient's body while the medical tool and auxiliary tool reach sufficiently inside the body. In such cases, there is thus no need to increase a surgical incision.

In some examples, the receptacle may be a through-hole. Optionally, the appendage may comprise a tubular or annular portion defining the through-hole. Optionally, the tubular or annular portion may be made of a resilient material, such that the auxiliary medical device can be received with a friction fit. In more alternatives, the receptacle may be open having e.g. a substantially C-shaped or U-shaped portion.

In some examples, the appendage may be made from a rigid material. In others, they may be made of a resilient material. A resilient material will allow a secure friction fit. Depending on the resiliency, auxiliary devices with slightly different dimensions can be fitted in the same through-hole. A single appendage may thus be suitable for fitting various different auxiliary medical devices, i.e. auxiliary medical devices having different diameters.

In some examples, the device may comprise an appendage that may be integrally formed with the base. In other examples, the appendage may be removably fixed to the base.

In some examples, a single base may comprise a first appendage and a second appendage, the first appendage having a receptacle configured to receive a first auxiliary medical device, and the second appendage having a receptacle configured to receive a second auxiliary medical device. In some surgical methods, two auxiliary devices may be needed simultaneously, e.g. a laser pointer and a surgical aspirator.

Depending on circumstances, devices comprising a base and several appendages of different types can be used, e.g. having different sizes and/or involving rigid and/or resilient materials may be foreseen.

In more examples, an appendage may be or comprise an antiskid strap attached to the base. Antiskid straps herein can be straps, bands, slings or loops that have a friction fit with an auxiliary medical case. In some of these cases, the straps may be provided with Velcro-type fasteners. In some cases, elastic bands may be foreseen as antiskid straps. The elastic bands achieve a friction fit when stretched due to the tendency to return to the natural relaxed state. In still further alternatives, combinations of appendages such as appendages integrally formed with the base and/or removably fixed to the bases and/or straps separated from the base may be foreseen.

In a further aspect, a kit for assisting in an open surgery is provided, the kit comprising a base configured to be mounted on a portion of a handheld medical tool, and an appendage configured to be removably fixed to the base and having a receptacle configured to receive an auxiliary medical device.

In some examples according to any of these aspects, the problems of illuminating may be addressed by a device attached to the medical tool or instrument, namely the base with an illumination device. The medical tool or instrument may in a direct manner and in proximity of the medical procedure provide the illumination needed to properly operate during the medical intervention or surgery.

The light source may enhance visualization of e.g. a surgical field—which is a key issue in surgery—while being lightweight and comfortable to use. The fact that the device or the kit can be mounted in a variety of medical instruments results in a versatile tool which may be added to a tool or instrument and used whenever convenient. Moreover, this permits to supplement the tools already at disposal and may highly improve the equipment performance at a reduced cost.

The device (and/or appendages) may be disposable and used only once. In other examples, the device or the kit may be used multiple times and may be configured to be sterilized after each use. Either way, contamination of the surgical field can effectively be avoided.

In some examples, the illumination device may be a LED. LEDs offer a cost-effective solution while keeping a high illumination standard. They require little maintenance and are cold, which avoids overheating or undesired temperature variations (for example, if a thermometer should be close to the light source). They may be provided with variable intensity control, so that they can adapt to changing demands. Alternatively, the illumination device may be a fiber-optic light. In further examples, the base may comprise two or more illumination devices.

In further examples, one or more incandescent light bulbs may be used.

In yet a further example, the base may comprise a central opening configured to be mounted around a portion of the handheld medical tool. Optionally, the base may comprise an O-ring or a diaphragm made of a relatively flexible material surrounding at least a portion of the central opening. This feature makes the device or kit adaptable to several handheld medical tools, particularly tools used in open surgery and in particular it may be adapted to be mounted on scalpel-like instrumentation.

In alternative examples, the base may comprise a hinge between a first half and a second half of the base, and wherein a biasing element forces the first and second half to contact each other. This feature allows moving conveying the external part of the base in the desired direction.

In yet other examples, the base may comprise a mounting ring arranged at or near an edge of the base for mounting on a medical tool.

During an open surgery, a surgeon may take a decision based on the specific circumstances whether to mount the base around the medical tool or not. As the surgery progresses, and if the situation changes, a surgeon may again judge to mount or dismount the base (and/or the appendages) from the tools he/she is using at that moment.

Flexibility or resiliency in the mounting arrangement makes it possible for the same base to be mounted on different tools.

In some examples, the device or the kit may further comprise a power cable for connecting to a power source. A plurality of controls and/or switches may be provided on the power source. As for switching the respective lamps on and off or activating the same, it can be advantageous if the lamps can be switched on individually or in groups. This results in a special option of controlling the light intensity on the one hand and the wavelength emitted on the other, as well as controlling the use of a further element, e.g. a laser pointer, that may further be provided at the base independently of the light sources or not. The device/kit can thus be adapted optimally to suit the respective application.

In some examples, the electrical cable comprises a plurality of fasteners for attaching to the handheld medical tool. The fasteners, which may be of several kinds, allow for a compact and handy mounting of the base onto the medical tool, so that the cable is not disturbing to the medical professional. In alternative examples, a plurality of fasteners may be attached to the medical tool, e.g. to a handle portion of the medical tool. For example, eyelets may be used for guiding the electrical cable.

The several feasible configurations may be adapted to the requirements of a plurality of procedures and/or applications, depending on the most useful and frequent uses. Thus, in some examples the further auxiliary device may be a sensor, a smoke and/or liquid evacuator, an ultrasonography sensor or another imaging device (e.g. video or photo camera).

In some examples, such a kit may comprise a first appendage configured to be removably fixed to the base and having a first receptacle configured to receive a first auxiliary medical device, and a second appendage configured to be removably fixed to the base and having a second receptacle configured to receive a second auxiliary medical device, wherein the first receptacle is of a different size or shape than the second receptacle.

Such a surgical kit comprises different appendages for fitting different auxiliary devices or different types of auxiliary devices. The base may comprise a first fastening element, and the appendages comprise a second fastening element, wherein the first and second fastening elements are configured to mate. In some cases, a single fastening element is provided for coupling with either the first or the second appendage. In some other cases, the base comprises a first and a third fastening element for coupling with the first and the second appendage simultaneously.

In some examples, a laser pointer may be mounted on the base such that when the base is attached to the handheld medical tool, the laser pointer is directed substantially towards a distal end of the handheld medical tool. The device or the kit may further comprise a power supply to power the laser pointer.

According to this aspect, a tool for pinpointing biological tissue of body parts of interest is provided in proximity of a bodily cavity. Furthermore, the laser pointer may be easily controlled without distracting the medical professional.

According to another aspect, a device for illuminating a medical procedure is provided. The device may include a base that is attachable to a handheld medical tool, an illumination device mounted on the base, a laser pointer mounted on the base such that when the base is attached to the handheld medical tool, the laser pointer is directed substantially towards a distal end of the handheld medical tool, and further includes a connection for connecting to a power supply to feed the illumination device and the laser pointer.

In yet a further aspect, a method for replacing a first auxiliary medical tool mounted in a receptacle of an appendage of a device for assisting in open surgery, when a base of the device is mounted on a portion of a handheld medical tool is provided. The method comprises providing the handheld medical tool together with the appendage supporting the first auxiliary medical tool in a surgery position; retracting the handheld medical tool from the surgery position; removing the first auxiliary medical tool; mounting a second auxiliary medical tool on the device for assisting in open surgery; and positioning the handheld medical tool in the surgery position. In accordance with this aspect, the method is carried out during an open surgery.

Herein, the surgical position is to be understood as a position in which the handheld medical tool protrudes beyond the incision in the skin of the patient to be able to perform a surgical action.

In accordance with this aspect, in examples, as the surgery progresses, and when the situation changes, a surgeon may judge to mount or dismount different auxiliary medical devices to the appendage, thus being able to use different combinations of tools rather rapidly during an open surgery. In a laparoscopic surgery, such procedures would be much more complicated since the surgical tool is further away from the surgeon.

In some examples, removing the first auxiliary medical tool may comprise removing the appendage from the device for assisting in open surgery. In some of these examples, mounting the second auxiliary medical tool on the device for assisting in open surgery comprises attaching a second appendage to the device for assisting in open surgery. Substituting one auxiliary medical tool for another auxiliary medical device may thus involve changing an appendage to quickly dismount and mount auxiliary medical tools. In other examples, a first auxiliary medical device may be removed from an appendage and a second auxiliary medical device may be fixed attached to the same appendage.

In yet a further aspect, a method for changing an auxiliary medical tool mounted in a receptacle of an appendage of a device for assisting in open surgery, when a base of the device is mounted on a portion of a first handheld medical tool is provided. The method comprises providing the first handheld medical tool together with the appendage supporting the first auxiliary medical device in a surgery position; retracting the first handheld medical tool from the surgery position; removing the device for assisting in open surgery from the first handheld medical tool; providing a second handheld medical tool; mounting the device for assisting in open surgery on the second handheld medical tool; and positioning the second handheld medical tool in the surgery position. In accordance with this aspect, the method is carried out during an open surgery.

In accordance with this aspect, during an open surgery, a device for assisting in open surgery may be removed from the principal handheld medical tool and then be attached to another handheld medical tool while still carrying the same auxiliary medical tools. Particularly, in the case the device comprises a base having a central opening for being mounted around a portion of the handheld medical tool (e.g. comprises a ring or diaphragm of flexible material), the device can be slid off the medical tool and be slid back onto a different medical tool. In laparoscopic surgeries, such a change would be much more complicated.

In yet a further aspect, a device for illuminating a medical procedure is provided, this device comprising: a base that is attachable to a handheld medical tool, an illumination device mounted on the base; and optionally a power supply to feed the illumination device. The illuminating device according to this aspect may incorporate one or more of the features described in connection with the other aspects. For example:

The handheld medical tool may be an electric scalpel. The illumination device may be one or more LEDs or fiber-optic light. The base may also comprises two or more illumination devices, optionally diametrically opposed illumination devices.

Optionally, the base may comprise a central opening configured to be mounted around a portion of the handheld medical tool. And in some cases, the base may comprise a ring made of a relatively flexible material (e.g. rubber or silicone gel or a combination thereof) surrounding the central opening.

In some cases, the power supply can comprise a battery mounted within a housing of the base. In other cases, the power supply can comprise an electrical cable configured to be connected to a power source.

In some examples of this illumination device, a further auxiliary device for use during a medical procedure may be mounted on the base, and optionally further including a switch to selectively activate the further auxiliary device. Such an auxiliary device may be a temperature sensor, e.g. a thermometer or an infrared radiation sensor, a spectrophotometer, a flow meter, a video or photo camera, a laser pointer or a suction device. Several of these could also be combined.

In yet a further aspect, an electrical scalpel is provided comprising an elongate shaft having a receptacle at or near the distal end of the elongate shaft, a blade configured to be received in the receptacle, and an illumination device as hereinbefore described mounted on the receptacle. In particular, the illumination device may be removably mounted on the receptacle.

BRIEF DESCRIPTION OF THE DRAWINGS

Non-limiting examples of the present disclosure will be described in the following, with reference to the appended drawings, in which:

FIGS. 7A and B show a further example of a device for assisting in an open surgery substantially as hereinbefore described.

DETAILED DESCRIPTION OF EXAMPLES

Handheld medical devices may include a variety of tools or instruments for applications in several fields. Such tools generally may comprise a handle portion or grip portion near a proximal portion of an elongated shaft and a working tool at a distal end of the shaft. For example such a tool can be an electrical scalpel or electrocautery knife which can be used in electro surgery. Other tools for medical treatment include further surgical tools, or tools in dentistry or orthodontics.

Electrosurgery is commonly used in dermatological, gynaecological, cardiac, plastic, ocular, spine, ear-nose-throat (ENT), maxillofacial, orthopedic, urological, neuro- and general surgical procedures as well as certain dental procedures. Electrosurgery is performed using an electrosurgical generator (also referred to as power supply or waveform generator) and a hand piece including one or several electrodes, sometimes referred to as a radiofrequency knife (RF knife).

Most of the examples of the present disclosure are shown in combination with an electrical scalpel. It should be clear however that the same and similar devices may be used in combination with other handheld medical tools. Other suitable medical tools include e.g. orthodontic and dental tools, probes, surgical graspers or tweezers, and surgical retractors. Most of the examples of the present disclosure are adapted and suitable for tools and procedures in which the illumination device or further auxiliary device do not enter completely into a bodily cavity, but rather stay outside the cavity or barely enters the cavity.

Examples of the present disclosure are generally configured for open surgeries wherein an opening is created or has been created in the skin of a patient.

Figure 1A:
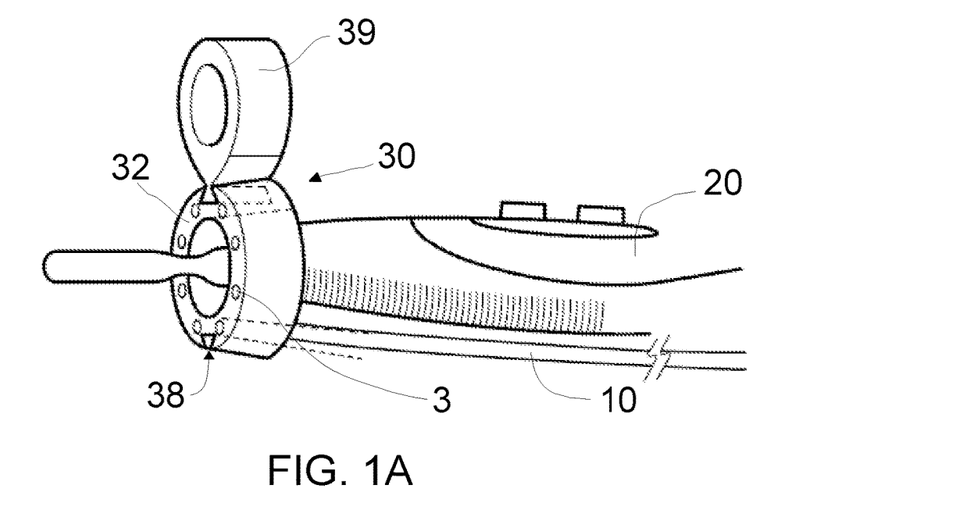
FIG. 1A schematically illustrates an example of a device for assisting in an open surgery procedure in combination with an electrical scalpel.
Figure 1B:
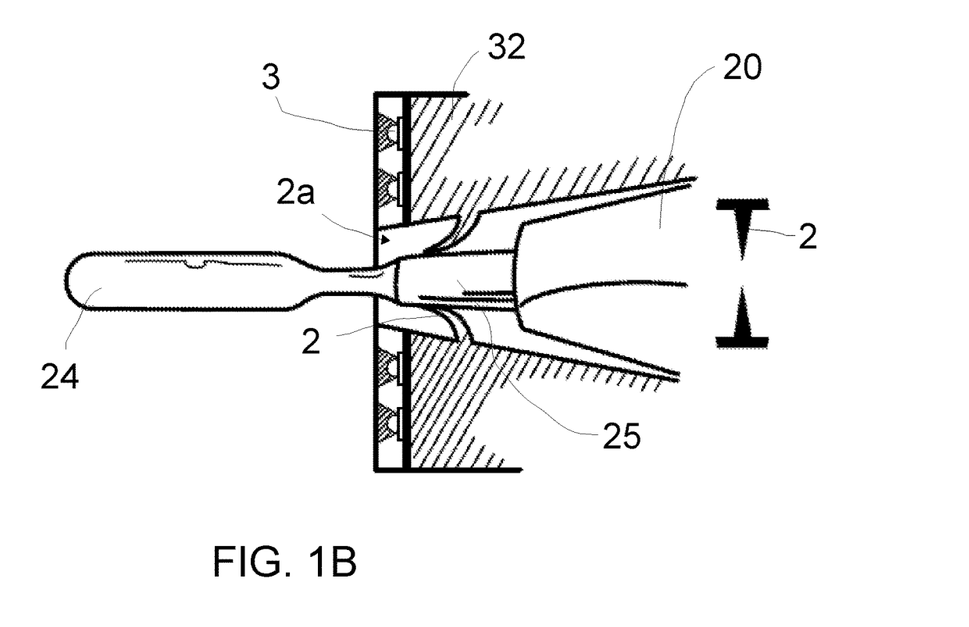
FIG. 1B illustrates a cross-sectional view of the device on the scalpel of FIG. 1A.

FIGS. 1A and 1B show an example of a kit or a device 30 for illuminating and assisting in a medical procedure, e.g. an open surgery, in combination with a handheld surgical tool. In this example, the handheld surgical tool is an electrical scalpel, which comprises an elongate shaft 20, having a receptacle 25 with a distal open end. The elongate shaft 20 may be held by a medical professional near a proximal end of the shaft. The proximal portion of the shaft 20 may have an ergonomic shape configured for gripping or handling. The gripping portion may extend from a proximal end to approximately a mid-portion of the shaft. The ergonomic shape may be adapted for a pencil grip.

The receptacle 25 of the electrical scalpel is configured to receive e.g. an electrocautery blade 24. The receptacle 25 may be made from an electric insulating material. The receptacle 25 may be made from a rubbery or polymeric material.

A power supply system for powering the scalpel, and a cable connecting a proximal end of the shaft with the power supply system may generally also be provided. A power switch allows turning on and off the power supply or otherwise regulating the power flow.

The kit or device 30 for assisting in open surgery in this example comprises a cylindrical base 32, which has a central opening 2a configured to be mounted around a portion of the handheld medical tool, for instance, around the receptacle 25. Thus, the base 32 can be positioned by introducing the receptacle 25 into the central opening 2a. As a result, the base is positioned distally with respect to a handle or gripping portion of the medical tool. The cylindrical base in some examples may have a diameter of e.g. approximately 1 cm, 1.5 cm or 2 cm.

Figure 1C:
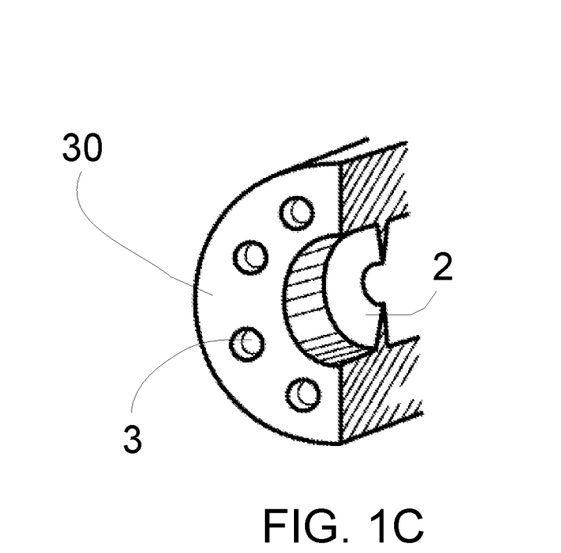
FIG. 1C schematically illustrates a detail of a device according to the example of FIG. 1A.
Figure 1D:
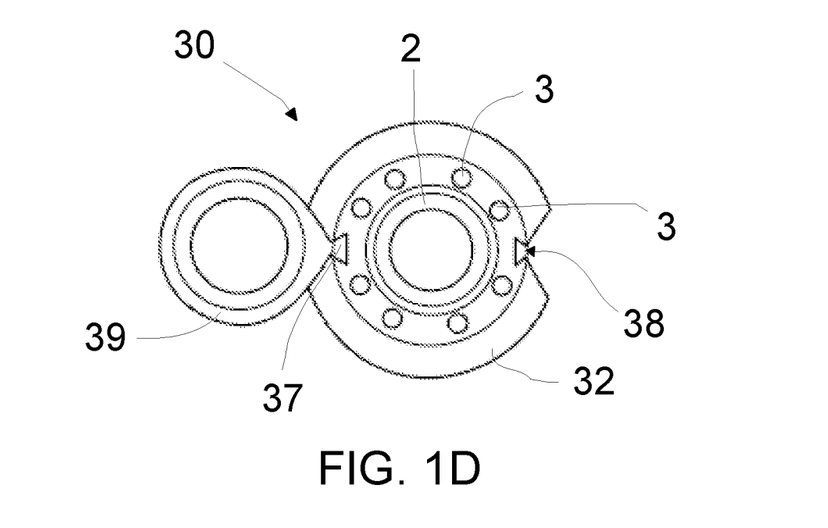
FIG. 1D illustrates a frontal view of the device of the example of FIG. 1A.

This is also illustrated in FIGS. 1C and 1D.

In this example, eight LEDs 3 are provided. Because of their distal position with respect to the hand of a medical professional, the hand cannot create any shadows. The LEDs may be strategically positioned so that regardless of the precise orientation of the scalpel, sufficient light is provided to the surgical field. In other examples, different numbers of LEDs may be provided.

The position on the receptacle 25 of the electrical scalpel thus makes visualization possible, but at the same time does not prevent access of the scalpel to the surgical procedure. The device can be positioned sufficiently proximally such that in case of small bodily openings or cavities, it stays outside of the patient.

In this case, the base has a generally round, rather flat frustoconical shape. Nevertheless, the base might have any geometry as long as it would be suitable for its purpose. An example of geometry requirements might include being light enough to keep the ensemble illumination device-medical tool manageable and not being too sharp or too bulky as to hamper the practitioner while using said ensemble.

In this example, the base 32 comprises a diaphragm 2 surrounding the central opening 2a. Alternatively, an O-ring may be used. The diaphragm 2 may be made of a relatively flexible material, so that it can adapt to several handheld medical tools. As the base 32 is pressed against or pulled away from the receptacle 25 of the shaft, the diaphragm 2 can deform to admit or release the receptacle 25 from the central opening 2a. Moreover, the flexibility of the diaphragm may adapt to a certain range of distal end diameters or geometries in a variety of handheld medical tools. This provides versatility to the kit/device, so that it may be used on different handheld medical tools according to need.

The kit or device 30 also has a connection for connecting to the power source, namely a cable 10 connecting a rear part of the base 32 with a power source. Some switches in a control panel may allow to control the different systems on the device, e.g., turning them on and off, individually or simultaneously.

At the rear part of the base, a power supply module (not shown) receives electrical power from the connection (i.e. cable 10) and feeds whatever devices are mounted on the base. In this case, illumination devices 3 are powered. However, in a further example, a laser pointer may also be integrated in the base, e.g. arranged in between the illumination devices. Alternatively, one of the shown illumination devices may be replaced with a laser pointer. The power supply may thus also receive electrical power from the same source.

Infrared laser pointers or green laser pointers may be useful. The integration of a laser pointer in the assisting and illuminating device offers several advantages compared to the normal use of pen-size laser pointers. The laser pointer may in some examples be turned on and off through switches provided at the power source or at the cable without the need for the practitioner to use a hand each time that he needs the laser pointer. Moreover, he or she may thus use the laser with better precision than if having to ask someone else to do so.

In addition, conventional laser pointers are unsterile, so that precautions must be taken in order to avoid contamination of the surgical field. In the examples of the present disclosure, the laser pointer is part of an assisting device that may be orderly sterilized and thus be treated as any other medical instrumentation. In particular, such a feature is an advantage in the medical practice, since it may lower the risk for contamination of the surgical area, and as a consequence of undesired complications during the patient's treatment.

In examples, the rear side of the base may comprise a printed circuit board which acts as a control system for the device.

The light sources according to examples of the present disclosure may be, e.g., a light emitting diode (LED), a fiber-optic light, incandescent light bulbs or other. The light source may be shaped and/or oriented to promote projection of light toward the area where the blade 24 is being used. As for the choice of one type of light source or the other, a choice may be made in accordance with circumstances balancing e.g. energy consumption, light output, color temperature and light source life (including lumen maintenance).

LEDs offer advantages for the surgical environment such as bright and highly uniform illumination. Its superior thermal management enables both high intensity light output and a long life (they yield a durability of e.g. 50,000 hours of LED headlight versus 3,000 to 7,000 hours of a fiber-optic headlight). Another advantage is the low replacement cost of single LED lamps. Fiber-optic light, instead, has the features of being a thin and flexible material, which may be an advantage for certain applications. These are the most common light sources for medical applications in the market nowadays, due to their well-suited technical features. However, other light sources might be considered for being implemented in the device or kit, depending on the user's requirements and/or limitations.

If fiber optic light is used, an additional fiber optic cable may be provided from the base to a light source. In examples, wherein only fiber optic light is provided (i.e. no laser pointer of further auxiliary device), no power supply would be needed on the base.

In the example of FIG. 1, the kit/device 30 comprises a base 32 and an appendage 39 removably fixed to the base 32. The base 32 in this example has two dovetail slots 38 which are diametrically opposite to each other. The appendage 39 has a suitable protrusion 37 with a shape complementary to the slot 38 to be slidably fitted in the slot 38. In this example, two appendages may be fitted to the base 32 at the same time.

In examples, the protrusion may be slightly larger than the slot such that a friction fit is established. A friction fit is one of the ways in which it may be ensured that the appendage does not move in an undesirable manner with respect to base 32.

Each of the appendages has a through-hole which serves as a receptacle for receiving an auxiliary medical tool. In this case, the "primary" medical tool is the electrical scalpel. The auxiliary medical tool may be any tool which may be used during an open surgery in combination with the electrical scalpel. Examples include:
  a video or photo camera,
  a laser pointer (for pinpointing tissue. A laser might in examples be integrated in the base. In other examples, it is an auxiliary device fitted in the appendage),
  sensors comprising thermometers, flow meters or the like. The sensors may be arranged at any suitable location in the base. A suitable position for placing sensors such as thermometers or flow meters would be on the side of the base which more easily can be in contact with the body tissue. An infrared radiation sensor may be used for determining temperature differences between tissues which may indicate vascularization. A flow meter may be based on ultrasound technology. The (ultrasonic) flow meter specifically in an implementation on an electrical scalpel may serve to locate blood vessels. A further or alternative sensor that may be incorporated in the device for the same purpose is a spectrophotometer.
  an irrigator (in case of electrocoagulation),
  a radioactive probe (e.g. when dissecting a tumor), or a liquid/gas aspirator (e.g. for aspirating smoke development when cutting using the scalpel).

In the latter case, such an aspirator may be combined with a REIMS spectrometer to immediately analyze the smoke. See FIG. 6A In examples, the auxiliary medical device or tool supports and/or enhances the functioning of the medical tool on which the device is mounted.

Figure 2A:
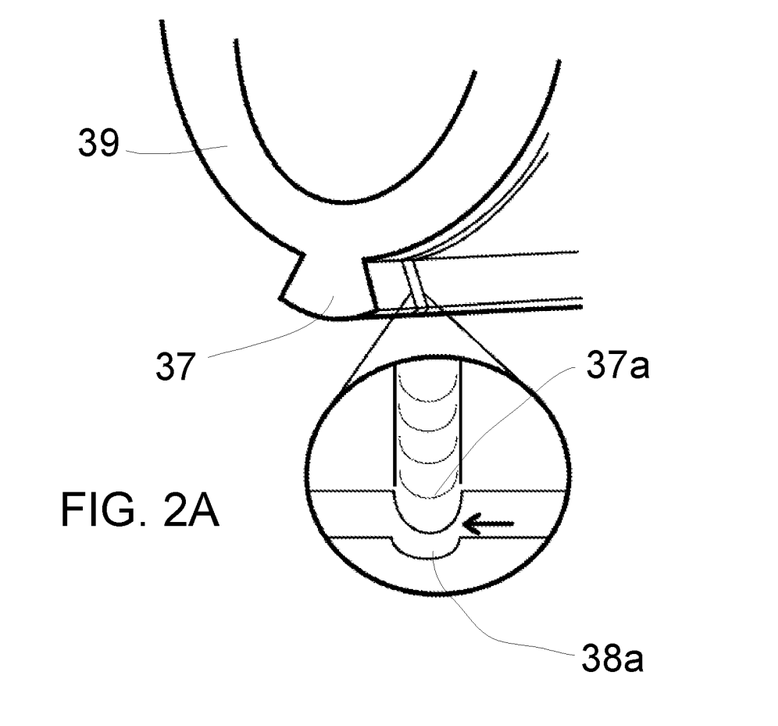
FIGS. 2A and 2B schematically illustrate details of examples of devices for assisting in open surgery.
Figure 2B:
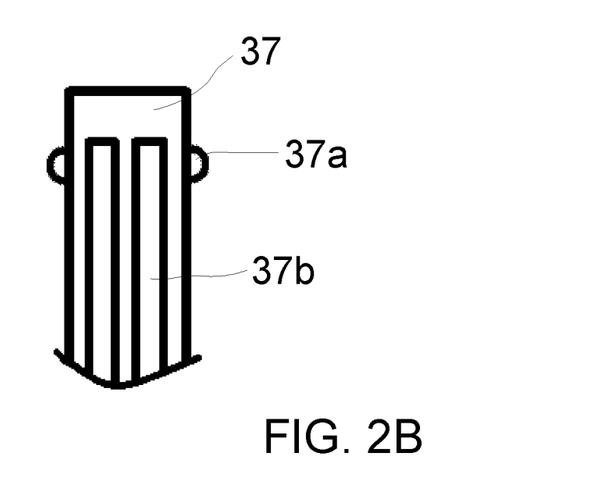

FIGS. 2A and 2B illustrate details which may be incorporated in examples of the devices (or kits) for assisting in an open surgery. FIG. 2A illustrates that the protrusion 37 which is configured to mate with the slot 38 may have one or more local protuberance 37a which may fit in complementary local recesses 38a along slot 38. The engagement of the protuberance 37A in local recess 38A can ensure that the appendage 39 is fitted to the base 32 in the correct position and stays in that position.

In examples, the engagement of the protrusion 37 into the slot 38 may further provide electrical power to provide energy supply to the auxiliary medical device being received in the appendage.

FIG. 2B illustrates that in examples, the base may have a portion that functions as an electrical connector. In the example of FIG. 2B, a bottom portion of the appendage may incorporate conductive stripes 37b. If or when the base is provided with electrical power, the same electrical power can be made available for e.g. an auxiliary device mounted in the appendage.

In yet further examples, a portion of the appendage may be shaped as an electrical plug (or socket) and the base may comprise a complementary socket (or plug), again to provide electrical power to an auxiliary medical device through the base.

Figure 3A:
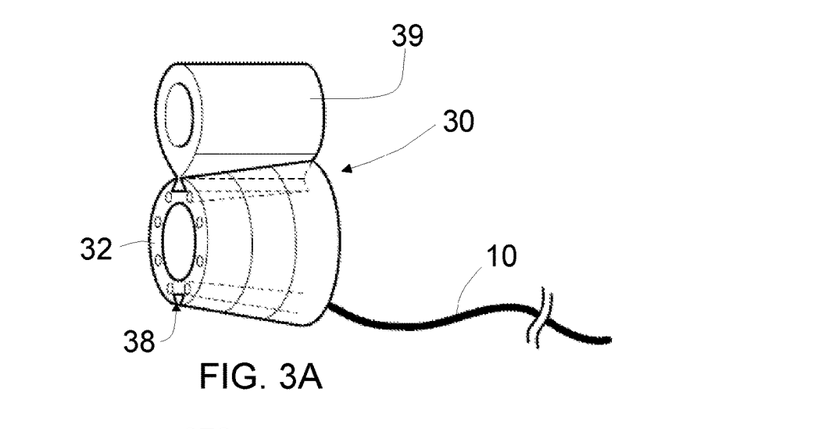
FIGS. 3A-3C schematically illustrate different views of a further example of a device for assisting in an open surgery.
Figure 3B:
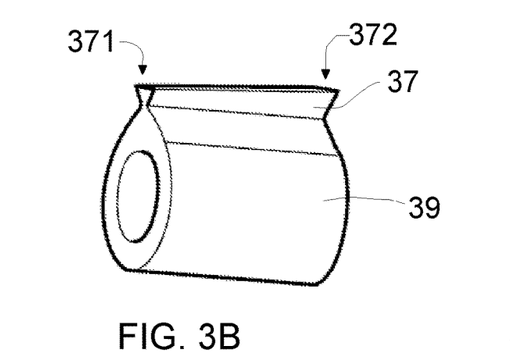
Figure 3C:
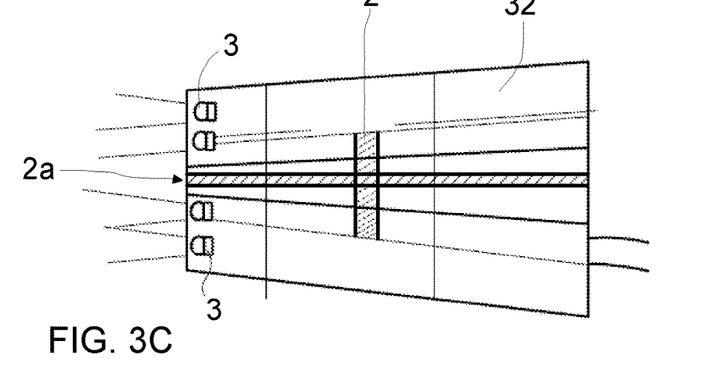

FIGS. 3A-3C schematically illustrate different views of a further example of a device or kit for assisting in an open surgery. FIG. 3A illustrates an example of a device/kit for assisting in open surgery which has an increased length as compared to the example of FIG. 1. Depending on which handheld medical tool is used as "primary" surgical tool, the geometry of the base 32 and kit/device 30 may be adapted to fit to the tool. Also in this example, the base 32 tapers outwardly from a distal end to a proximal end.

FIG. 3B illustrates that, similarly, the protrusion 37 may taper outwardly from a distal end 371 to proximal end 372. An aspect of such a tapered protrusion (and mating slot) is that the correct position of the appendage 39 with respect to the base 32 can be ensured.

Again in this example, two appendages can be fitted to base 32. In further examples, a base may be provided that is configured for only a single appendage, or for three or more appendages. In still further examples, the appendage(s) may be integrally formed with the base. See FIGS. 7A-8B.

Figure 4A:
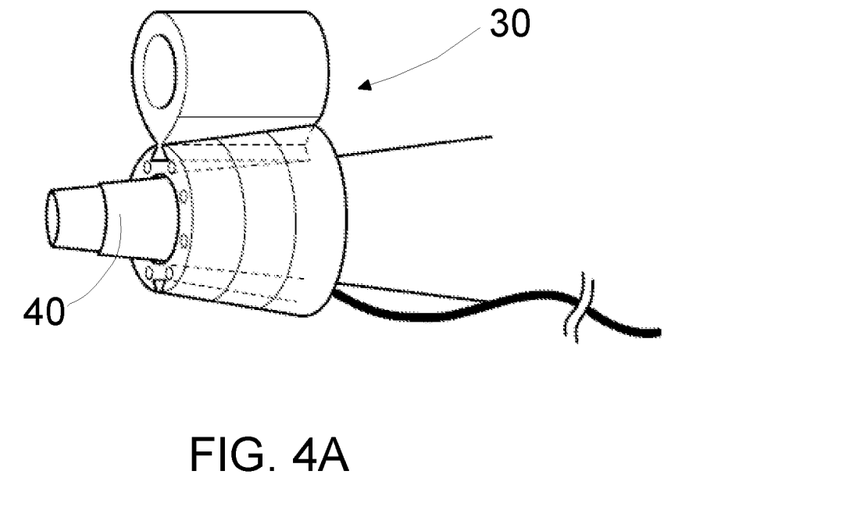
FIGS. 4A and 4B schematically illustrate a further example of a device for assisting in open surgery with different handheld medical devices and auxiliary medical tools.
Figure 4B:
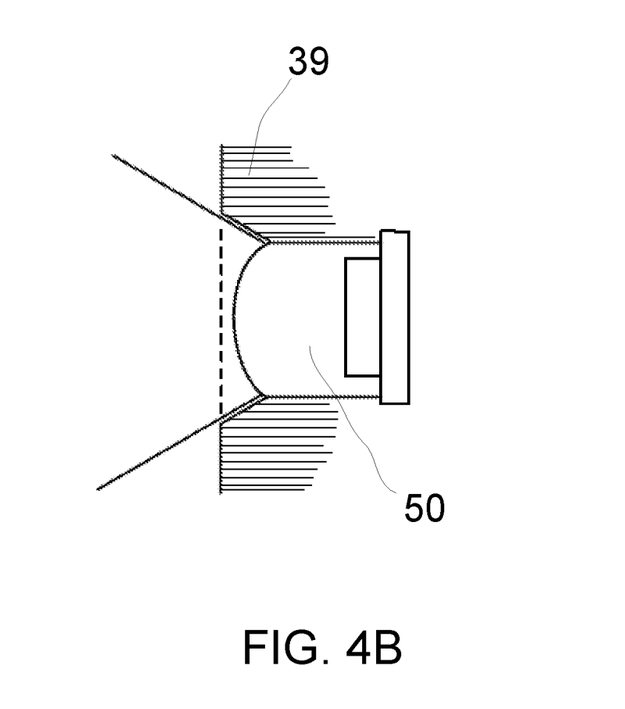

FIGS. 4A and 4B schematically illustrate a further example of a kit/device for assisting in an open surgery with different handheld medical devices and auxiliary medical tools. In FIG. 4A, the kit/device 30 is fitted to an ultrasonic scalpel 40.

FIG. 4B serves to illustrate that complementary to the LEDs 3, an additional illumination device 50, e.g. an incandescent light bulb may be temporarily positioned in appendage 39 when increased illumination is required. The further illumination device in this case thus acts as the auxiliary medical tool.

Figure 5A:
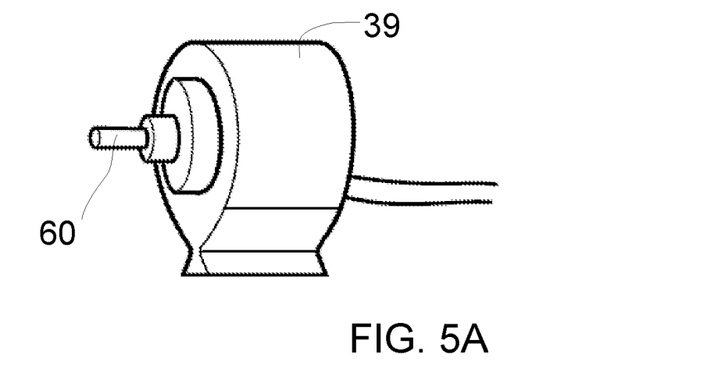
FIGS. 5A-5C schematically illustrate different auxiliary medical devices which may be used with examples of the devices for assisting in open surgery.
Figure 5B:
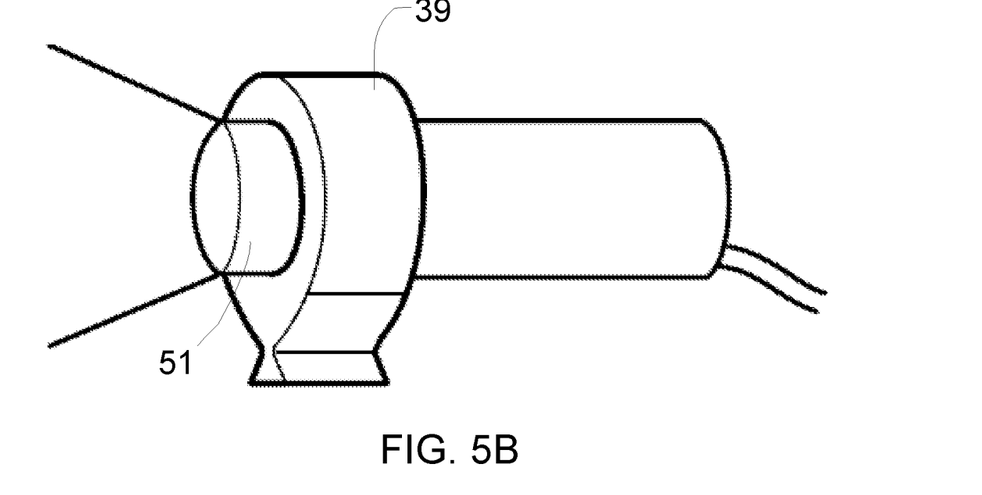
Figure 5C:
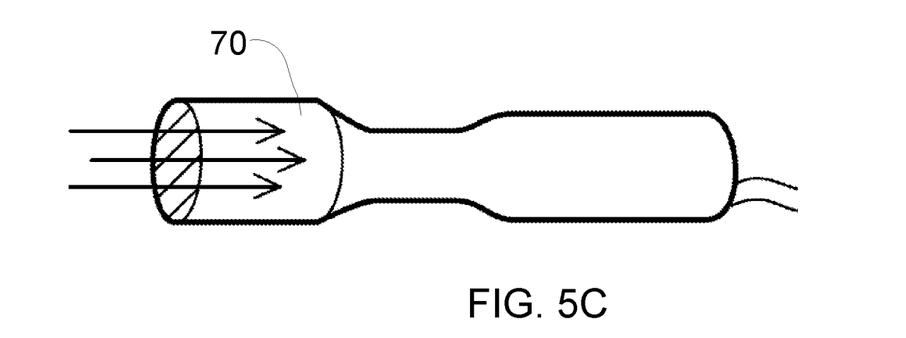

FIGS. 5A-5C schematically illustrate three further auxiliary medical devices which may be used with examples of the kits/devices for assisting in an open surgery. Particularly FIG. 5A shows a laser pointer 60. In particular, an infrared laser or green laser pointer are used in operating rooms. In the examples of the present disclosure, such laser pointers or laser pens may be inserted in the receptacle of appendage 39 such that they point towards a distal end of the primary medical tool.

FIG. 5B serves to illustrate that on occasions, it might be preferable to have light 51 of a different wavelength, e.g. infrared or UV light instead of white light. On such occasions, a suitable LED may simply be inserted in an appendage 39 to provide the required illumination. And FIG. 5C serves to illustrate that on occasions, it might be preferable to have a radioactive probe in order to measure radioactive radiation and thus precisely determine the position of cells and tissue affected by cancer.

Figure 6A:
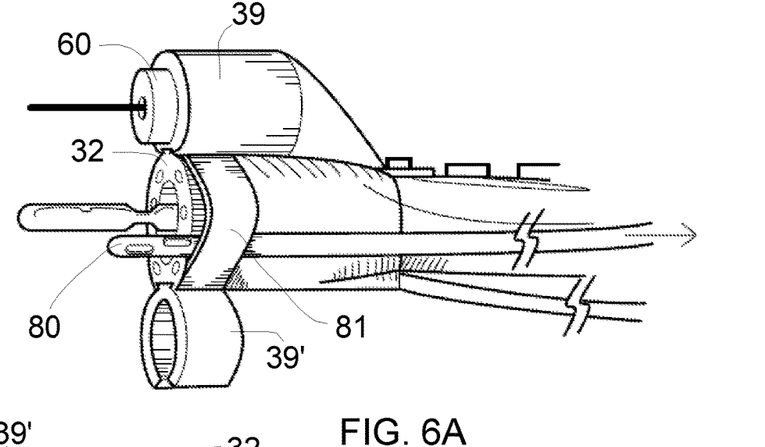
FIGS. 6A-6C show another example of a device for assisting in an open surgery.
Figure 6B:
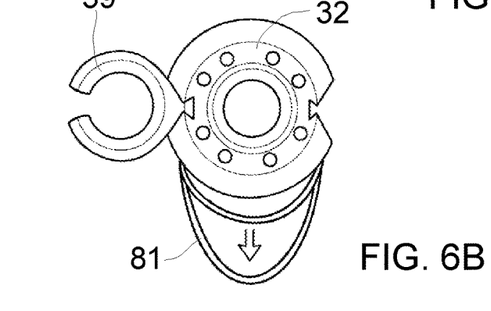

FIGS. 6A-6B show a kit or device according to a different example comprising two appendages 39 and 39. The example shown in FIG. 6A thus differs from that of FIG. 1A in that a second appendage 39' is also removably fixed to the base 32 substantially as explained in connection with FIG. 1A. Furthermore, a laser pointer 60 is fitted in the appendage 39 substantially as explained in connection with FIG. 5A. Further in this example, the second appendage 39' is open, i.e. it has a substantially C-shaped portion, as clearly shown in FIG. 6B which shows a partial front view of the kit/device illustrated in FIG. 6A.

If the portion with the substantially C-shaped cross-section is sufficiently closed and/or has sufficient resiliency, an auxiliary medical device can be positioned in the corresponding through-hole. The auxiliary medical device may in examples be mounted with a snap-fit.

And the kit/device of FIG. 6A further differs from that of FIG. 1A in that a tube 80 aspirating the generated smoke and leading towards a REIMS spectrometer may also be attached to the base by an elastic strap 81 that is connected to the base 32, between the first 39 and second 39' appendages.

FIG. 6B illustrates how an elastic band or strap can function as an appendage. The elastic band can be forced to elongate to create sufficient space for fitting an auxiliary medical device. The auxiliary medical device in this sense is then clamped between the base 32 and the elastic band.

Figure 6C:
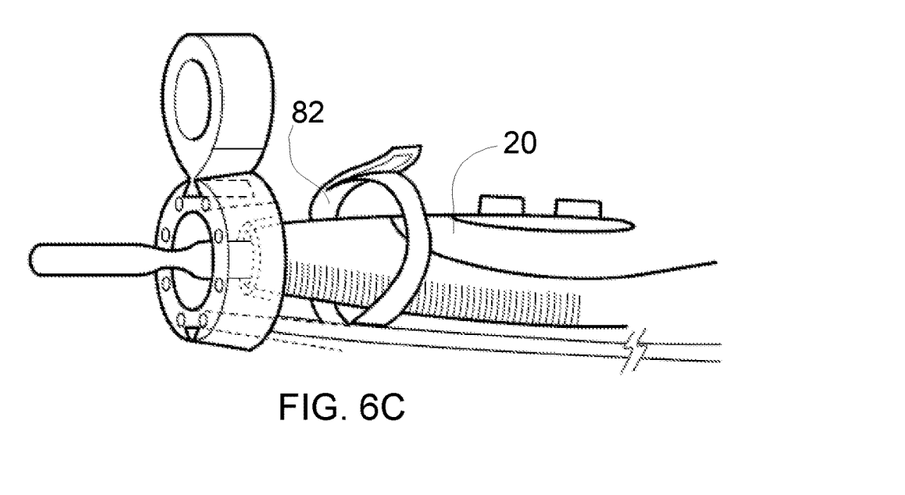

FIG. 6C shows that in further alternatives a strap 82 provided with a Velcro-type fastener may be foreseen e.g. for attaching the electrical cable to the shaft 20 of the electrical scalpel. The electrical cable thus will not hinder movements of the surgeon or of the medical devices.

Figures 7A, 7B:
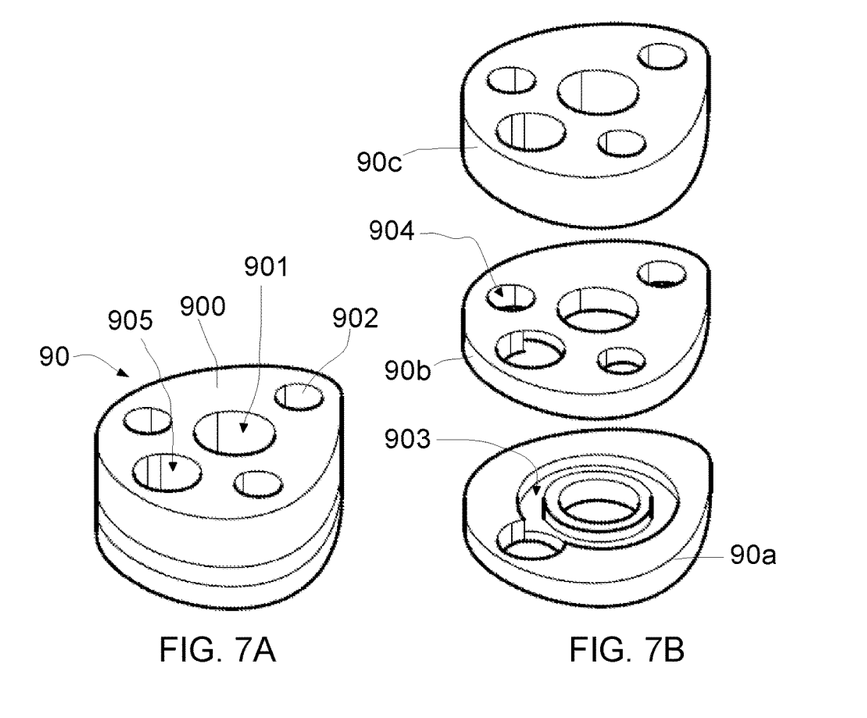
Figures 8A, 8B:
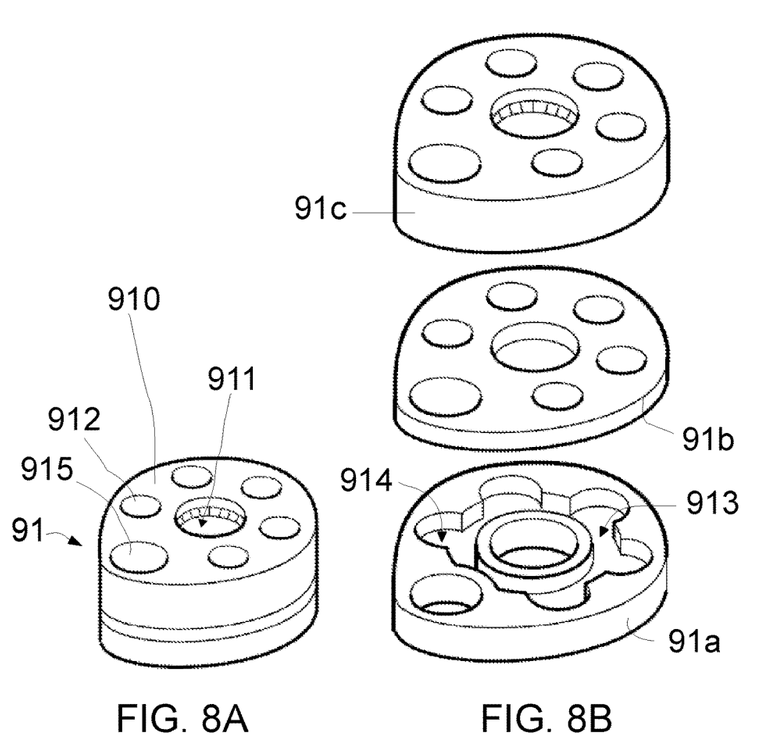
FIGS. 8A and 8B show a still further example of a device for assisting in an open surgery substantially as hereinbefore described.

FIGS. 7A-8B show two alternative devices for assisting in an open surgery. FIGS. 7A and 8A show perspective views of this examples and FIGS. 7B and 8B show exploded view of the same. These examples differ from the examples above in that an appendage 90 (FIG. 7), or 91 (FIG. 8) is integrally formed with the substantially cylindrical base 900 and 910.

In both cases the base 900 and 910 comprises a central opening 901 and 911 for receiving a handheld medical tool such as the electrical scalpel of the example of FIG. 1A. Alternatively, other handheld medical tools in particular surgical tools may be foreseen.

Further in these examples, an auxiliary through-hole working channel 905, 915 may be integrally formed with the base 900, 910. Alternatively, the working channel may comprise a C-shape or U-shape such that it can grip an auxiliary medical tool, substantially as explained in connection with FIG. 6A or 6B.

The example of FIGS. 7A and 7B comprises three LEDs 902 equidistantly arranged at 120° angles between them around the central opening 901. And the example of FIGS.

8A and 8B comprises five LEDs 912 equidistantly arranged (at 72° angles between them) around the central opening 911.

FIGS. 7B and 8B further show that these examples are made from three pieces 90a, 91a; 90b, 91b and 90c, 91c made of e.g. a resilient material. Polyamide is one of the materials suitable for this case.

In the example of FIG. 7B, spaces 904 for accommodating LEDs 902 are provided between pieces 90a and 90b, and a grooved space 903 for housing e.g. any required wiring is further defined between pieces 90a and 90b. In the example of FIG. 8B, piece 91a is provided with spaces 913 for accommodating the LEDs 912. Furthermore, a grooved space 914 for housing required wirings is defined between pieces 91a and 91b.

In this example, the device may be relatively easy manufactured and assembled. For assembly, the three pieces may be glued together. In these examples, the device incorporates base and appendage in a single integrally formed body, but in other examples may be separate elements to be assembled just prior or during surgery.

In these examples, a power cable (not shown) for connecting to a power source may further be attached to e.g. a rear side of respectively pieces 90a or 91a so as to supply power to the LEDs. In some cases a laser pointer may be integrated in the base 900, 910 such that it points towards a distal end of a primary medical tool that may be placed around the central opening 901, 911. The laser pointer may be arranged e.g. replacing one of the LEDs or in between LEDs substantially as explained in connection with FIG. 1.

In any of the examples disclosed herein, different types of light may be used. In some implementations, white light may be preferred.

In some examples, a device or kit substantially as hereinbefore described mounted or mountable on a medical tool may include illumination systems configured to emit light in different ranges of wavelength. In some examples, the wavelength of an illumination system may be varied in use.

In any of the hereinbefore described examples, the cable 10 providing electrical power to the kit/device 30 may comprise a fastener for attachment of the cable to the shaft 20 of the electrical scalpel. Suitable fasteners include: a mounting clip, adhesives, clamps, cable ties, or Velcro™ fasteners, to mention some possibilities. In some examples, a mounting clip may be attached to the shaft through a snap-on connection. The mounting clip can also have an opening to receive the cable or connection to the power source. The clip may be positioned at a variety of places on the shaft 20. A clip according to this example could be attached to the shaft 20 by, e.g., sliding the clip onto the shaft. Analogously, the clip may be easily removed from the shaft by sliding it off the shaft. A plurality of mounting clips may be used, depending on the length and geometry of the medical tool.

In any of the hereinbefore described examples, the device may have a timer linked to the lighting system provided. The device may be programmed to automatically turn off the light(s) and/or automatically disconnect electrical power after a predetermined period of time.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

The invention claimed is:

1. A device for assisting in an open surgery, comprising:
a base configured to be mounted on a portion of a handheld medical tool selected from a group consisting of an electrical scalpel, an ultrasonic scalpel, a radiofrequency knife, a surgical clamp, a sealant and a cautery;
an illumination device mounted on the base such that when the base is attached to the handheld medical tool, the illumination device is directed towards a distal end of the handheld medical tool; and
an appendage to the base having a receptacle configured to receive an auxiliary medical device.

2. The device according to claim 1, wherein the receptacle is a through-hole.

3. The device according to claim 2, wherein the appendage comprises a tubular or annular portion defining the through-hole.

4. The device according to claim 1, wherein the appendage has a substantially C-shaped or U-shaped portion defining the receptacle.

5. The device according to claim 1, wherein the appendage is or comprises a strap defining the receptacle.

6. The device according to claim 1, wherein the appendage is made of a resilient material and the auxiliary medical device is secured to the appendage by a friction fit.

7. The device according to claim 1, wherein the appendage is integrally formed with the base.

8. The device according to claim 1, wherein the appendage is a first appendage and the auxiliary medical device is a first auxiliary medical device, the device further comprising a second appendage to the base having a second receptacle configured to receive a second auxiliary medical device.

9. The device according to claim 8, wherein the first appendage and second appendage are arranged in diametrically opposite positions of the base.

10. The device according to claim 8, wherein the appendage comprises an antiskid strap attached to the base for housing an auxiliary medical tool.

11. The device according to claim 1, wherein the base comprises a ring or diaphragm having a central opening for being mounted around a portion of the handheld medical tool.

12. The device according to claim 11, wherein the ring or diaphragm is made of a relatively flexible material surrounding the central opening.

13. The device according to claim 1, wherein the receptacle is configured to receive an auxiliary medical tool selected from the group consisting of a surgical aspirator or smoke/liquid evacuator, a laser pointer, a handheld ultrasound system, an irrigator for electrocoagulation, a further illuminating device, a radioactive probe, a camera or a sensor.

14. The device according to claim 1, further comprising a power supply.

15. The device according to claim 1, further comprising an electrical cable configured to be connected to a power source.

16. The device according to any of claim 1, wherein the base comprises two or more illumination devices.

17. The device according to claim 1, wherein the illumination devices are LEDs or fiber optic lights.

18. The device according to claim 14, wherein the power supply is a battery.

19. The device according to claim 12, wherein the flexible material is rubber or silicone gel or a combination thereof.

20. A device for assisting in an open surgery, comprising:
- a base configured to be mounted on a portion of a handheld medical tool;
- an illumination device mounted on the base such that when the base is attached to the handheld medical tool, the illumination device is directed towards a distal end of the handheld medical tool; and
- an appendage to the base having a receptacle configured to receive an auxiliary medical device,
- wherein the appendage is removably fixed to the base.

21. The device according to claim 20, wherein one of the base and the appendage comprises a slot and
- the other of the appendage and the base comprises a protrusion with a shape complementary to the slot.

* * * * *